(12) United States Patent
Shorter et al.

(10) Patent No.: US 6,197,067 B1
(45) Date of Patent: Mar. 6, 2001

(54) LOWER LIMB PROSTHESIS WITH AN INJECTION MOLDED FLANGED SHIN PORTION

(75) Inventors: John Jeffrey Shorter, Itchenor; Victor James Woolnough, North Waltham; Graham James Harris, Basingstoke, all of (GB)

(73) Assignee: Chas. A. Blatchford & Sons Limited, Hampshire (GB)

( * ) Notice: Subject to any disclaimer, the term of this patent is extended or adjusted under 35 U.S.C. 154(b) by 0 days.

(21) Appl. No.: 09/011,847
(22) PCT Filed: Aug. 14, 1996
(86) PCT No.: PCT/GB96/01982
§ 371 Date: Apr. 3, 1998
§ 102(e) Date: Apr. 3, 1998
(87) PCT Pub. No.: WO97/06754
PCT Pub. Date: Feb. 27, 1997

(30) Foreign Application Priority Data

Aug. 18, 1995 (GB) .................................... 9516993

(51) Int. Cl.$^7$ .................................. A61F 2/66; A61F 2/60
(52) U.S. Cl. ................................................. 623/53; 623/27
(58) Field of Search ................... 623/47–52, 27, 623/53

(56) References Cited

U.S. PATENT DOCUMENTS

| | | |
|---|---|---|
| 4,547,913 | 10/1985 | Philips . |
| 4,911,724 | 3/1990 | Fikes . |
| 4,959,073 | 9/1990 | Merlette . |
| 5,116,381 | 5/1992 | Palfray . |
| 5,156,631 | 10/1992 | Merlette . |
| 5,219,364 * | 6/1993 | Lloyd ................................. 623/33 |

FOREIGN PATENT DOCUMENTS

| | | |
|---|---|---|
| 0 454 524 A1 | 10/1991 | (EP) . |
| 690657 | 9/1930 | (FR) . |
| 2 114 447 | 8/1983 | (GB) . |
| 91/15169 | 10/1991 | (WO) . |

* cited by examiner

*Primary Examiner*—David H. Willse
(74) *Attorney, Agent, or Firm*—Barnes & Thornburg

(57) ABSTRACT

An artificial limb has an endoskeletal shin component which is of generally constant H-shaped cross section and is formed by injection molding from thermoplastics material. In a preferred embodiment, the limb has a foot keel which is integrally molded with the shin component. The keel also has upper flanges which are contiguous with anterior and posterior flanges of the shin component. Such a limb can be made light in weight yet strong in terms of resistance to transverse bending moments, and can be inexpensively produced. The constant cross section of the shin component allows it to be cut to a required length and clamped to an upper limb component.

38 Claims, 3 Drawing Sheets

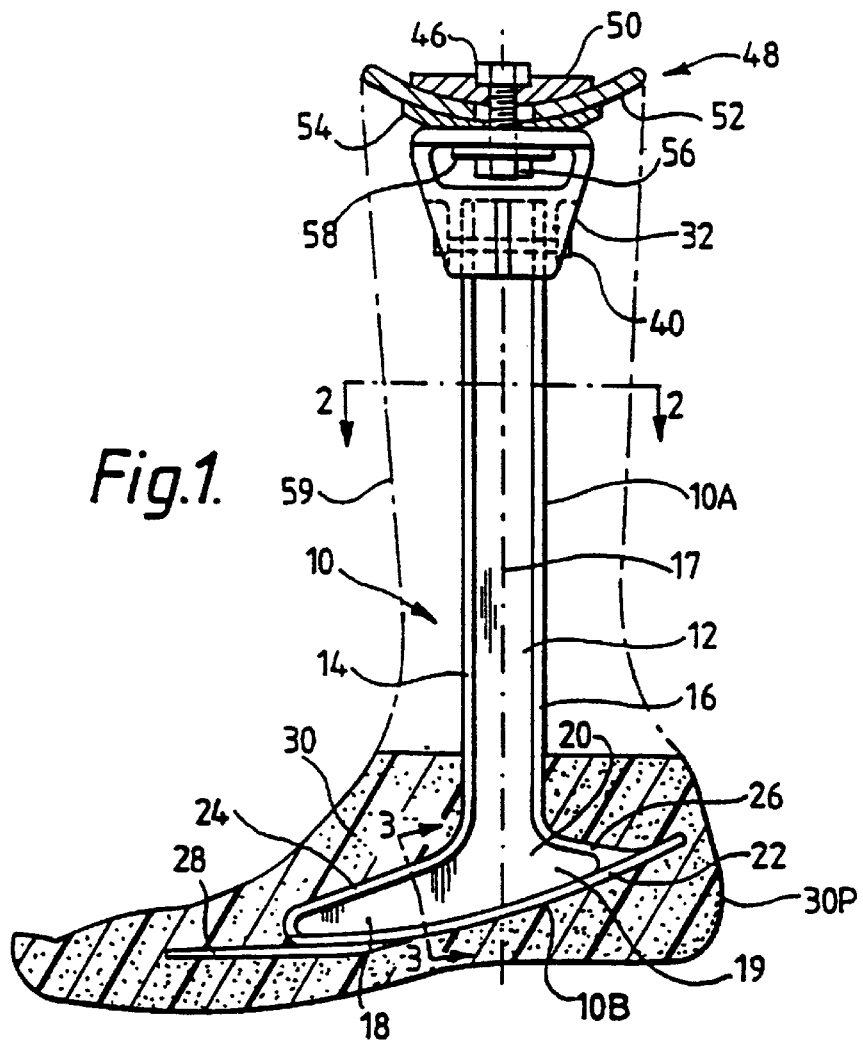
Fig.1.
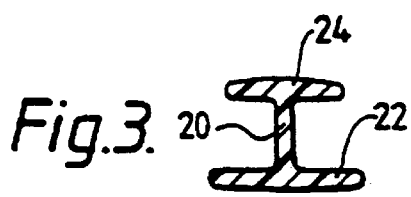
Fig.2.
Fig.3.

LOWER LIMB PROSTHESIS WITH AN INJECTION MOLDED FLANGED SHIN PORTION

CROSS-REFERENCE TO RELATED APPLICATIONS

This application is a U.S. national application of international application serial No. PCT/GB96/01982 filed Aug. 14, 1996, which claims priority to British Serial No. 9516993.4 filed Aug. 18, 1995.

This invention relates to an artificial limb and particularly to a lower limb prosthesis which is inexpensive to manufacture.

Much of the development of artificial limbs has been to produce a prosthesis which is as light as possible yet is strong and functionally sophisticated. As a result, such prostheses tend to use expensive materials and manufacturing techniques. There is a need for a prosthesis which can be manufactured inexpensively and in large quantities, but which is still lightweight, robust, and comfortable to wear and use.

According to a first aspect of this invention, there is provided an endoskeletal artificial limb comprising a load-bearing elongate structural member which is injection-moulded from a thermoplastics material, and has a longitudinal web and at least one integral longitudinal flange arranged transversely of the web. Preferably, at least a portion of the member is straight and of constant cross-section, with at least two integral longitudinal flanges located along opposite edges of the web, the cross-section being of H- or I-shape.

Such a limb can be dimensioned so as to be lightweight, yet strong in terms of resistance to transverse bending moments. It has the additional advantage of having some torsional resilience which, in the case of a lower limb prosthesis, reduces shear forces acting between the amputee's stump and the stump socket.

In a particular embodiment of the invention the artificial limb is a lower limb prosthesis in which the structural member comprises at least a shin portion of substantially constant cross-section. In this particular embodiment, the structural member includes a foot keel with anteriorly and posteriorly extending portions, integrally formed in one piece with the shin portion in a single injection-moulding operation. The keel may have a web extending in the anterior-posterior direction, co-planar and contiguous with the web of the shin portion. The keel may also have a flange extending lengthwise in the sole of the foot, integrally formed at the distal edge of the keel web. The flange extends transversely on both sides of the keel web. Preferably this sole flange is curved in the longitudinal direction of the foot so as to have a convex lower surface.

The keel may extend both anteriorly and posteriorly relative to the shin portion, and may also have upper flanges which, in the case of the shin portion having two longitudinal flanges, are contiguous with those flanges, the upper flanges curving proximally from the foot to merge directly into the flanges of the shin portion.

The portion of constant cross-section preferably extends to the proximal end of the elongate structural member, the limb further comprising a clamp fitted to the said end to enclose the longitudinal web and flange end and for mounting to an upper limb component. The clamp is a thermoplastics component having a recess of a cross-section which corresponds to that of the structural member, the component thereby enclosing the proximal end of the member. The clamp may have cut-outs extending in the longitudinal direction of the structural member on opposite sides thereof, the cut-outs being spanned by respective clamping bolts extending between oppositely directed outer faces of the clamp whereby clamping forces can be exerted by tightening the bolts to pinch the or each flange of the structural member. The or each clamping bolt has the effect of distorting or deforming the material of the clamp to grip the structural member.

Different upper limb components may be attached to the structural member by the clamp. In the case of a lower limb prosthesis, the clamp may be attached to or form a distal part of a knee assembly. Alternatively, it may connect the structural member to a stump socket, with or without an intervening alignment device. If the clamp is required to be detachable from an upper or proximal limb component, it may comprise a clamp housing for the structural member and a proximal plate which forms a bridge on the proximal side of the clamp housing, the bridge being integrally formed with the housing as a single injection-moulded component. Another possibility, in the case of a prosthesis for an above-knee amputee, is to form the upper part of the shin as a knee housing which has an integral clamp housing for receiving the proximal end of the structural member.

In another embodiment, the clamp is replaced by a housing having a recess with a cross-section corresponding to the cross-section of the structural member, the recess being so dimensioned that the structural member is an intimate fit within the recess. The member may be held in place simply by friction, or a latch feature or by an adhesive.

In keeping with the concept of a prosthesis with the minimum number of components and with minimum cost, in the case of a lower limb prosthesis the foot is preferably a unitary foam structure moulded in situ over the foot keel referred to above. The central longitudinal axis of a straight shin portion may pass through the foot at a distance from the extreme posterior end of the foot which is equal to between 0.29 and 0.33 as a proportion of the total length of the foot. More particularly, the proportion is between 0.30 and 0.32.

A toe-break strip made of, for instance, a resilient polyurethane material may be bonded to the distal face of the keel to extend anteriorly of the keel.

With regard to the material of the structural member, this is preferably a fibre-loaded thermoplastics material such as nylon loaded with glass fibres (typically less than 10 mm in length). The proportion of fibres by weight is preferably between 35% and 60%, as a percentage of the total weight of the material.

The above-described limb can be cheaply produced by injection-moulding a limited range of structural members with different keel sizes, and moulding a foam foot in situ over the keel of each member with the member held in a predetermined position relative to the mould for the foot, to form a unitary shin and foot assembly. At the fitting stage, a shin and foot assembly of the required size is selected, the shin portion is cut to a required length and joined at the proximal end to a stump socket or, in the case of a prosthesis for an above-knee amputee, to a knee joint which is, in turn, connected to a socket. An alignment device may be included between the socket and the shin portion. If required, a cosmetic flexible foam covering may be slid over the shin portion.

The invention also includes, according to a second aspect thereof, a method of making an artificial limb comprising selecting a unitary shin and foot assembly having a shin portion comprising a structural member which is injection-moulded from a thermoplastics material and which, over at least a proximal end portion is of constant cross-section having a web and at least one transverse flange, cutting the shin portion to a required length, securing the cut end of the shin portion in a receptacle, and securing the receptacle to a stump socket.

According to a third aspect of the invention, there is provided a shin component for an artificial limb comprising an injection-moulded thermoplastics structural member having a longitudinal web and at least one integral longitudinal flange extending transversely of the web.

According to a fourth aspect of the invention, a component for an artificial limb comprises a shin portion having a longitudinal web and at least one integral longitudinal flange extending transversely of the web, and a foot keel, the shin portion and the keel being integrally formed as a single-piece injection-moulded structural member.

The invention will now be described by way of example with reference to the drawings in which:

FIG. 1 is a side elevation of a lower limb prosthesis for a below-knee amputee;

FIG. 2 is a plan view of the main structural member of the prosthesis of FIG. 1, sectioned on the line 2—2 in FIG. 1;

FIG. 3 is a cross-section of the foot keel sectioned on the line 3—3 in FIG. 1;

Figure 4A:
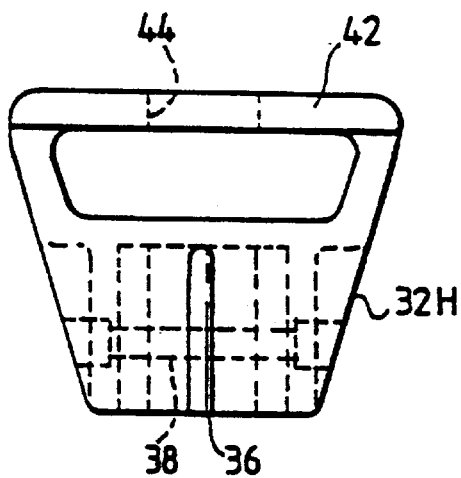
FIGS. 4A, 4B and 4C are respectively side, underside and front elevations of a proximal clamp for the below-knee prosthesis of FIG. 1.

Referring to FIG. 1 of the drawings, a lower limb prosthesis in accordance with the invention for a below-knee amputee has an internal structural member 10 comprising a shin portion 10A and a foot keel 10B integrally formed with the shin portion 10A. The structural member 10 is a one piece injection-moulded component made of a glass fibre loaded nylon material available from LNP Engineering Plastics (U.K.) Limited under the name VERTON. The shin portion is straight end of constant cross-section over its entire length, the cross-section being of H-shape, having a central longitudinal web 12 lying in a plane extending substantially in the anterior-posterior direction, and anterior and posterior flanges 14, 16 arranged along the edges of the web 12 and each extending in a medial-lateral direction. The cross-section of the shin portion 10A is more clearly visible in FIG. 2, which clearly shows the H-shape.

A shin portion having this configuration has high strength in the anterior-posterior and medial-lateral planes, yet is torsionally flexible to a limited degree, thereby allowing some rotation of the keel 10B about the central longitudinal axis 17 of the shin portion.

The depth of the shin portion 10A in the anterior-posterior direction is within the range of from 25 to 35 mm, and is preferably less than 32 mm. In the preferred embodiment shown in the drawings, it is 30 mm. The width of the member in the medial-lateral direction preferably has the same dimensional limitations. The web and flange thickness is substantially uniform and within the range of from 2.5 mm to 5 mm. A uniform 4 mm thickness is preferred.

As will be seen in FIGS. 1, 2, and 3 together, the keel 10B forms an anterior bridge portion 18 and a posterior heel portion 19 both integrally formed with the shin portion 10A, the bridge portion extending into a metatarsal region of the foot, i.e. a region corresponding to the position of the metatarsal bones in the natural foot, and also has a central web 20 extending in the anterior-posterior direction, which is co-planar with the web 12 of the shin portion 10A and integrally formed with the latter. A sole flange 22 extends along the distal edge of the keel web 20 and transversely on both sides of the latter. Flange 22 is curved to form a lower surface which is convex in the anterior-posterior direction so that to the posterior of the shin axis 17, the flange 22 is inclined upwardly to the rear to a greater extent than to the anterior of the axis 17. The flange 22 is typically 40 mm in width to provide a stable base for the prosthesis.

Along the upper edge of the keel web 20 there is an upper anterior flange 24 which is contiguous with the anterior flange 14 of the shin portion and extends around an anterior end of the keel 10B to meet the lower flange 22. A similar flange 26 extends in the posterior direction contiguously from the flange 16 of the shin portion to meet the lower flange 22 in the heel region of the foot.

The anterior end of the keel 10B lies behind the location corresponding to the ball of the foot in a natural foot, and a keel extension in the form of a resilient plastics strip 28, shown only in FIG. 1, is attached to an anterior portion of the keel to extend into the toe region of the foot. Extension 28 is made of a thermoplastics elastomer available from Dupont under the Registered Trade Mark HYTREL, and is bonded to the lower or distal surface of the flange 22 of the keel 10B using double-sided adhesive tape.

As shown in FIG. 1, the keel 10B and a small part of the shin portion 10A is encased in a moulded foot 30. The material used for the foot moulding is a resilient foam material. The configuration of the keel, with the lower flange 22 inclined upwardly in the heel region of the foot results in a greater thickness of foam beneath the keel 10B in the heel region than in the instep region, the foot thereby corresponding to the conventional SACH foot configuration. The curved lower flange 22 provides for a continuous rolling movement of the keel 10B during the stance phase of the walking cycle, with the toe-break strip 28 providing resilient bracing for the forefoot at toe-off.

In this embodiment, the distance between the posterior extremity 30P of the foot 30 and the axis 17 is about 0.305 times the overall length of the foot 30.

Figure 4B:
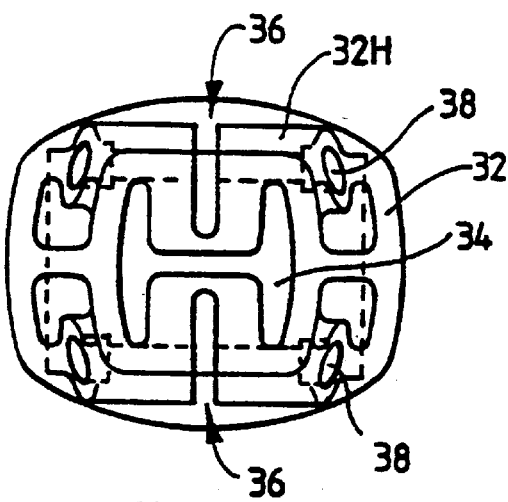
Figure 4C:
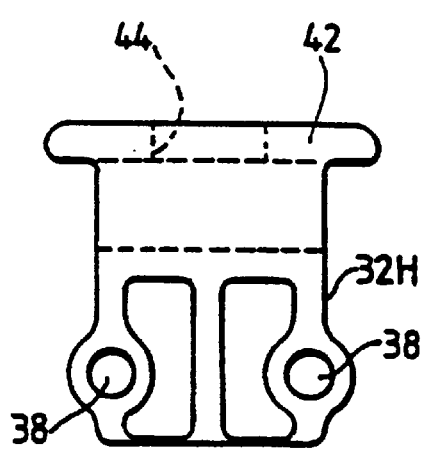

Since the shin portion 10A is of constant cross-section, it can be sawn to a required length at the time of patient-fitting, and secured to a stump socket 52 by means of a clamp 32, as shown in FIG. 1. Referring to FIGS. 4A–4C, the clamp 32 is an injection-moulded component, preferably moulded from the same material as the shin and keel, and has two integrally formed parts. The first part is a clamp housing 32H having a distally open recess 34 of a cross-section corresponding to the cross-section of the shin portion 10A, a will be seen by comparing FIG. 4B with FIG. 2. In this embodiment, the material of the housing 32H completely surrounds the recess 34 without a break. However, cut-outs 36 are formed on each side of the housing, on opposite sides of the central arm of the recess "H", these cut-outs 36 extending from the medial and lateral surfaces of the clump housing 32H to within a short distance of the central part of the recess 34. Bores 38 penetrate the housing 32H on opposite sides of the recess 36 perpendicularly to the cut-outs 36 and, in this embodiment, in an anterior-posterior direction. When the shin portion 10A is fitted into the recess 34, bolts 40 (see FIG. 1) received in the bores 38, are used to compress the sides of the housing 32H which, being flexible, deform and pinch the edges of the shin portion flanges 14, 16 to secure the shin portion 10A in the housing 32H. The fact that the cut-outs 36 are blind means that continuous supporting blocks of material remain between the flanges 14 and 16 of the shin portion 10A. The bolts 40 also act as tie bars to prevent failure of the housing 32H when subject to an anterior-posterior moment.

The upper part of the clamp 32 in this embodiment is a mounting plate 42 formed as a bridge spaced proximally from the housing 32H and connected to the latter on the anterior and posterior sides. The top surface of the plate 42 is perpendicular with respect to the axis 17, and is penetrated by a central hole 44 for receiving a coupling bolt 46 (see FIG. 1) for attaching the clamp 32 to upper parts of the prosthesis, in this case a conventional alignment device 48. Mounting of the stump socket 52 in the alignment device is effected by trapping the distal end of the socket between a socket plate 50 and a part-spherical cup 54 bearing against the proximal surface of the clamp plate 42. Bolt 46 is secured by means of a nut 56 distally of the bridge 42. The clamping load produced by the nut and bolt is distributed across the plate 42 by a large washer 58. Using a plate 42 as described above, in combination with a spacer having a corresponding planar lower surface extending over the majority of the proximal surface of the plate, together with a large washer bearing against the distal surface of the plate 42 produces a connection able to withstand the bending moments applied to the prosthesis by the patient despite the use of a thermoplastics material for the clamp 32.

Interposing an alignment device 48 between clamp 32 and the socket is not essential. In a simpler version of the prosthesis, the bridge plate 42 may be directly connected to the stump socket.

A cosmetic foam covering 59 (shown in chain lines in FIG. 1) is provided around the shin portion 10A, abutting the foot cosmesis 30.

The limb described above is preferably manufactured and supplied in component form, i.e. as a shin and foot component, a clamp, an alignment device, and a stump socket. The shin and foot component is supplied as a single piece, i.e. with the foot 30 moulded in situ on the distal end of the structural member 10. At the fitting stage, the shin portion 10A is cut to a required length, clamp 32 is fitted and secured at the proximal end, the alignment device, if present, is fitted, together with a stump socket. In the preferred embodiment, the prosthesis has no mechanically moving parts, and no detachable fastening below the proximal end of the shin portion 10A. In addition, it has no metallic parts below the proximal end of the shin portion.

The function of the bolts 40 in the clamp 32 is not only to secure the shin portion 10A, but also to reinforce the clamp housing 32H to prevent splitting of the thermoplastics material from which it is made. However, the clamp 32H can, if required, be made of stronger material and the bolts 40 omitted, the shin portion 10A being secured in the housing 32H by other means, e.g. bonding.

Figure 5:
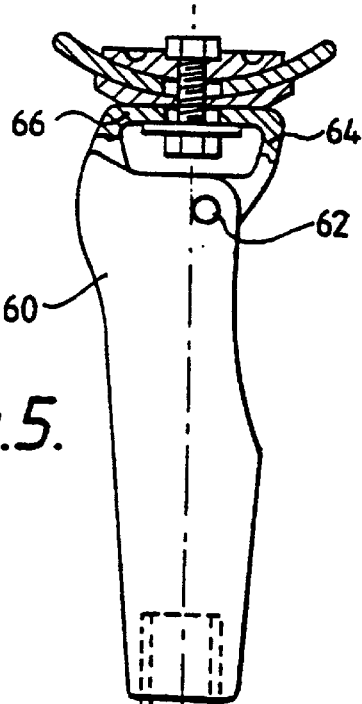
FIG. 5 is a side elevation of a lower limb prosthesis for an above-knee amputee.

The shin and foot assembly (10, 30) described above can be used in a prosthesis for an above-knee amputee, as shown in FIG. 5. In this case, shin portion 10A is secured by clamping or bonding in a knee cradle component 60. Cradle 60 rotates about a knee axis 62 with respect to a knee chassis 64 which has a bridge plate 66 similar to plate 42 of the clamp 32 described above. An alignment device and stump socket are secured to place 66 in the same manner as described above for the below-knee prosthesis.

Knee cradle 60 may include a clamp housing at its distal end like housing 32H described above with reference to FIGS. 1, 4A, 4B, and 4C. The housing may be rotatable with respect to the cradle 60 to adjust toe-in or toe-out of the foot.

Figure 6A:
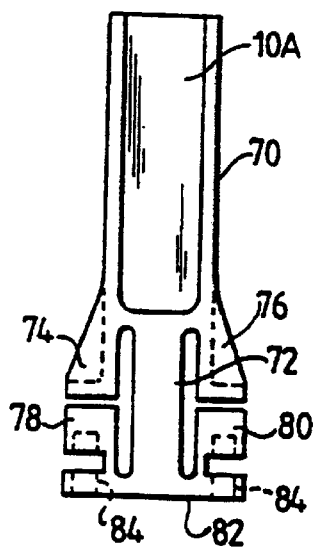
FIGS. 6A to 6C are side, front and plan views of a structural member for a lower limb prosthesis incorporating an ankle joint.
Figure 6B:
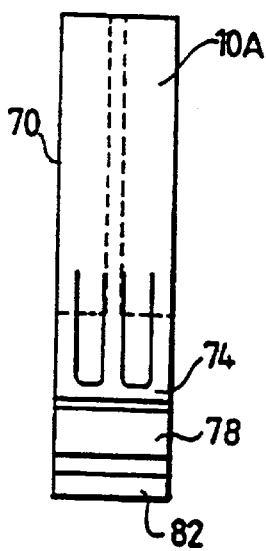
Figure 6C:
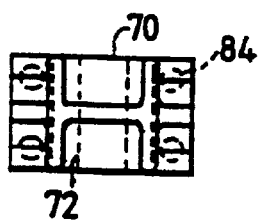

An ankle joint may be incorporated, as shown in FIGS. 6A to 6C which are views of an integral shin portion and ankle joint component 70 made of the glass-fibre loaded nylon material referred to above. In this case the lower end of the component 70 has flexible central hinge portion 72 which is of rectangular cross-section, being thinner in the anterior-posterior direction than in the medial-lateral direction to allow dorsi and plantar flexion. Anterior and posterior extensions 74, 76 of the shin portion 10A are in registry with and proximally spaced from stops 78, 80 adjacent the foot interface 82 to limit flexion in both directions as hinge portion 72 flexes under load.

In this case the combined shin and ankle component 70 is shown as being demountable from a foot keel (not shown) by means of bolts (not shown) which are received in four bores 84 in the foot interface 82. It is perfectly possible for the foot keel to be integral with the component 70.

In another embodiment of the invention, not shown in the drawings, the shin portion terminates at its distal end in a cylindrical boss integrally formed with the H-section, to allow clamping within a cylindrical sleeve forming part of an ankle joint, for example, or a SACH foot base.

What is claimed is:

1. An endoskeletal lower limb prosthesis comprising a load-bearing elongate injection-molded structural member made from a thermoplastics material, which member has a longitudinal web and a pair of integral longitudinal flanges extending transversely of the web to form a shin portion of H- or I- shaped cross-section, the said cross-section being substantially constant over at least a part which extends to a proximal end of the member.

2. A lower limb prosthesis according to claim 1, wherein the shin portion part which is of constant cross-section is also straight.

3. A lower limb prosthesis according to claim 1, wherein the web lies in an anterior-posterior plane.

4. A lower limb prosthesis according to claim 1, wherein the structural member includes an integral anteriorly-extending foot portion.

5. A lower limb prosthesis according to claim 1, wherein the structural member includes an integral posteriorly-extending heel portion.

6. A lower limb prosthesis according to claim 1, wherein the structural member is molded from a fiber-loaded thermoplastics material.

7. A lower limb prosthesis according to claim 1, wherein the structural member includes a foot keel integrally formed with the shin portion.

8. A lower limb prosthesis according to claim 7, wherein the keel has a central web extending in the anterior-posterior direction which is coplanar with the longitudinal web of the shin portion.

9. A lower limb prosthesis according to claim 8, wherein the keel extends anteriorly with respect to the shin portion and has an upper flange which is contiguous with one of the longitudinal flanges of the shin portion.

10. A lower limb prosthesis according to claim 8, wherein the keel extends anteriorly and posteriorly with respect to the shin portion and has a longitudinally convexly curved lower flange.

11. A lower limb prosthesis according to claim 10, wherein the shin portion integral longitudinal flanges are located along opposite respective edges of the web, and wherein the anteriorly and posteriorly extending portions of the keel have respective upper flanges which merge into respective ones of the said longitudinal flanges.

12. A lower limb prosthesis according to claim 1, further comprising a demountable clamp secured to the shin part of constant cross-section.

13. A lower limb prosthesis according to claim 12, wherein the clamp has a clamp housing including a distally opening recess of a cross-section corresponding to the cross-section of the shin part.

14. A lower limb prosthesis according to claim 12, wherein the clamp includes at least one tie bolt for tightening the clamp on the shin part.

15. A lower limb prosthesis according to claim 1, including a unitary shin and foot comprising a single piece shin portion and keel molding, and a molded foam foot encasing the keel.

16. A method of making a lower limb prosthesis comprising providing a plurality of unitary shin and foot assemblies, each assembly comprising an elongate injection-molded structural member made from a thermoplastics material, the member having a web and a pair of transverse flanges which form a shin portion of H- or I-shaped cross-section, at least a proximal part of the shin portion extending to the proximal end of the member being of substantially constant cross-section, selecting one of the assemblies, cutting the shin portion of the selected assembly to a required length, securing the cut end of the shin portion in a receptacle, and securing the receptacle to a stump socket.

17. A method according to claim 16, wherein the securing step comprises detachably clamping the shin portion in a clamp housing having a recess of a cross-section which corresponds to the said substantially constant cross-section.

18. A method according to claim 16, wherein the step of securing the receptacle to the stump socket includes coupling the receptacle to an alignment device with or without an intervening knee joint.

19. A component for lower limb prosthesis comprising an elongate injection-molded thermoplastics structural member having a longitudinal web and a pair of integral longitudinal flanges extending transversely of the web to form a shin portion of H- or I-shaped cross-section, the cross-section being substantially constant over at least part of the component, which part extends to a proximal end of the component whereby the component can be cut to a required length before being secured to an upper component of the prosthesis.

20. A component according to claim 19, wherein the shin portion is straight and of constant cross-section over substantially the whole of its length.

21. A component according to claim 19, wherein the structural member is formed of a fiber-loaded thermoplastics material.

22. A component according to claim 19, further comprising a foot keel, the shin portion and the keel being integrally formed as a single-piece injection-molded structural member.

23. A component according to claim 22, wherein the keel has a central web which is coplanar with the web of the shin portion and upper flanges which are contiguous with respective ones of the said longitudinal flanges.

24. A component according to claim 23, wherein the shin portion is straight and of constant cross-section over substantially the whole of its length.

25. A component according to claim 22, wherein the structural member is formed of a fiber-loaded thermoplastics material.

26. A component according to claim 21, wherein the length of the fibers in the structural member are mostly less than 10 mm in length.

27. An endoskeletal lower limb prosthesis comprising a load bearing elongate injection-molded structural member made from a thermoplastics material, which member comprises:
   a shin portion formed as a longitudinal web lying in an anterior-posterior plane and a monolithically formed longitudinal flange extending transversely of the web, and
   a foot keel having a central web which is coplanar and monolithically formed with the longitudinal web of the shin portion and of substantially the same width as the longitudinal web and with the keel extending anteriorly and having an upper flange which is contiguous with the said longitudinal flange of the shin portion.

28. A lower limb prosthesis according to claim 27, wherein the shin portion has integral longitudinal flanges which are located along opposite respective edges of the longitudinal web, and wherein the foot keel has both anteriorly and posteriorly extending portions with respective upper flanges which merge into respective ones of the said longitudinal flanges.

29. A lower limb prosthesis according to claim 27, wherein the keel has an integral longitudinally convexly curved lower flange.

30. A component for a lower limb prosthesis, comprising a shin portion having a monolithically formed longitudinal web and at least one longitudinal flange extending transversely of the web, and an anteriorly extending foot keel, wherein the shin portion and foot keel are monolithically formed as a single-piece injection-molded thermoplastics structural member, and wherein the foot keel has a central web of substantially the same width as the longitudinal web which is co-planar and monolithically formed with the longitudinal web of the shin portion and an upper flange which is contiguous with the said longitudinal flange.

31. A component according to claim 30, wherein the shin portion has integral longitudinal flanges which are located along opposite respective edges of the longitudinal web, and wherein the foot keel has both anteriorly and posteriorly extending portions with respective upper flanges which merge into respective ones of the said longitudinal flanges.

32. A component according to claim 30, wherein the keel has an integral longitudinally convexly curved lower flange.

33. An endoskeletal lower limb prosthesis comprising a load bearing elongate injection-molded structural member made from a thermoplastics material, which member comprises:
   a shin portion formed as a longitudinal web lying in an anterior-posterior plane and a monolithically formed longitudinal flange portion extending transversely of the web, and
   a foot keel having a central web which is coplanar and monolithically formed with the longitudinal web of the shin portion, the keel extending anteriorly and having an upper flange portion which extends generally antero-posteriorly and is contiguous with the said longitudinal flange portion of the shin portion such that said flange portions together form a contiguous flange.

34. A lower limb prosthesis according to claim 33, wherein the shin portion has integral longitudinal flange portions which are located along opposite respective edges of the longitudinal web, and wherein the foot keel has both anteriorly and posteriorly extending portions with respective upper flange portions which merge into respective ones of the said longitudinal flange portions to form respective continuous flanges.

35. A lower limb prosthesis according to claim 33, wherein the keel has an integral longitudinally convexly curved lower flange.

36. A component for a lower limb prosthesis, comprising a shin portion having a longitudinal web and at least one longitudinal flange portion extending transversely of the web, and an anteriorly extending foot keel, wherein the shin portion and foot keel are monolithically formed as a single-piece injection-molded structural member, and wherein the foot keel has a central web which is coplanar and monolithically formed with the longitudinal web of the shin portion and an upper flange portion which extends generally anteroposteriorly and is contiguous with said longitudinal flange portion such that said flange portions together form a contiguous flange.

37. A component according to claim 36, wherein the shin portion has integral longitudinal flange portions which are located along opposite respective edges of the longitudinal web, and wherein the foot keel has both anteriorly and posteriorly extending portions with respective upper flange portions which merge into respective ones of the said longitudinal flange portions to form respective contiguous flanges.

38. A component according to claim 36, wherein the keel has an integral longitudinally convexly curved lower flange.

* * * * *